US00PP07768P

United States Patent [19]

VandenBerg

[11] Patent Number: Plant 7,768

[45] Date of Patent: Jan. 14, 1992

[54] CHRYSANTHEMUM PLANT NAMED ROCHELLE

[75] Inventor: Cornelis P. VandenBerg, Salinas, Calif.

[73] Assignee: Yoder Brothers, Inc., Barberton, Ohio

[21] Appl. No.: 565,706

[22] Filed: Aug. 13, 1990

[51] Int. Cl.[5] ..... A01H 5/00

[52] U.S. Cl. ..... Plt./74

[58] Field of Search ..... Plt./74, 82.4, 74.1

*Primary Examiner*—Howard J. Locker

*Attorney, Agent, or Firm*—Foley & Lardner

[57] ABSTRACT

A chrysanthemum plant named Rochelle particularly characterized by its flat capitulum form; spooned daisy capitulum type; purple ray floret color; diameter across face of capitulum of 38 to 44 mm. when fully opened when grown as a pinched spray pot mum; very floriferous with excellent display of many small flowers; photoperiodic response to short days of 44 to 52 days; plant height of 18 to 25 cm. when grown as a pinched pot mum; small dark green foliage; and spreading and prolific branching pattern.

3 Drawing Sheets

The present invention comprises a new and distinct cultivar of Chrysanthemum, botanically known as *Dendranthema grandiflora,* and referred to by the cultivar name Rochelle.

Rochelle, identified as 86-667005, was originated from a cross made by Cornelis P. VandenBerg in a controlled breeding program in Salinas, Calif., in 1986.

The female parent of Rochelle was an unnamed seedling identified as 82-350002, and described as a purple spooned daisy spray pot mum having a flowering response to short days of 52 to 60 days under normal conditions, a plant height of 18 to 30 cm. with 1 to 2 applications of 2500 ppm B-9 SP and 15 to 16 long days after direct sticking of unrooted cuttings, a breaking action of 3 to 5 breaks per plant after pinch, and a semi-spreading plant habit. The flower size of the female parent is not available from breeding records.

The male parent of Rochelle was an unnamed seedling, identified as 83-S01002, and described as a yellow daisy spray pot mum having many very small flowers, each approximately 25 mm in diameter, a flowering response to short days of 46 to 55 days under normal conditions, a plant height of 25 to 33 cm. with 0 to 2 applications of 2500 ppm B-9 SP and 14 to 19 long days after direct sticking of unrooted cuttings, a breaking action of 5 to 9 breaks per plant after pinch, and a wide spreading habit.

Rochelle was discovered and selected as one flowering plant within the progeny of the stated cross by Cornelis P. VandenBerg in January 1987, in a controlled environment in Salinas, Calif.

The first act of asexual reproduction of Rochelle was accomplished when vegetative cuttings were taken from the initial selection in March 1987 in a controlled environment in Salinas, Calif., by technicians working under the supervision of Cornelis P. VandenBerg.

Horticultural examination of controlled flowerings of successive plantings has shown that the unique combination of characteristics as herein disclosed for Rochelle are firmly fixed and are retained through successive generations of asexual reproduction.

Rochelle has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice.

The following traits have been repeatedly observed and are determined to be basic characteristics of Rochelle, which, in combination, distinguish this Chrysanthemum as a new and distinct cultivar:

1. Flat capitulum form.
2. Spooned daisy capitulum type.
3. Purple ray floret color.
4. Diameter across face of capitulum of 38 to 44 mm. when fully opened, when grown as a pinched spray pot mum.
5. Very floriferous with excellent display of many small flowers.
6. Photoperiodic flowering response to short days of 44 to 52 days.
7. Plant height, with 22 to 25 long days after sticking unrooted cuttings, and with 1 to 2 applications of 2500 ppm B-9 SP, ranges from 18 to 25 cm. when grown as a pinched pot mum with 4 cuttings in a 15 cm. pot.
8. Small, dark green foliage.
9. Branching pattern is spreading and prolific, each plant having 5 to 7 laterals after pinch.

The accompanying photographic drawings show typical inflorescence and leaf characteristics of Rochelle, with the colors being as nearly true as possible with illustrations of this type.

Sheet 1 is a color photograph of Rochelle grown as a pinched spray pot mum with 4 cuttings in a 15 cm. pot.

Sheet 2 is a black and white photograph of three views of the inflorescence of Rochelle.

Sheet 3 is a black and white photograph showing the upper and under sides of the leaves of Rochelle at three stages of development (mature, intermediate and immature). Sheets 2 and 3 include a measuring tape in centimeters, thereby illustrating the dimensions of the flowers and leaves.

No commercial varieties known to the inventor can be compared with Rochelle. The combination of purple flower color, spooned daisy capitulum type, very high number of small flowers, small dark green foliage, and spreading and prolific branching pattern is unique, and is not represented in any commercial cultivar known to the inventor. The cultivar closest to Rochelle, although having different capitulum type and ray floret color, is the cultivar Papillon, disclosed in pending Plant patent application Ser. No. 07/435,825, now U.S. Plant Patent No. 7,435. Reference is made to attached Chart A, which compares certain characteristics of Rochelle to the same characteristics of Papillon.

Similar traits are capitulum form, small dark green foliage and spreading branching pattern. The ray floret color of Rochelle is purple, while Papillon has a red-purple ray floret color. Rochelle has a larger flower and an average of one lateral more after pinch when compared with Papillon.

When compared with both parents, Rochelle has a faster flowering response than either parent. Rochelle has a shorter plant height than either parent, requiring 22 to 25 long days after sticking to attain desired plant height, while both parents require 15 to 19 days after sticking to attain similar height. Breaking action of Rochelle is greater than that of the female parent, but comparable to the breaking action of the male parent.

In the following description color references are made to The Royal Horticultural Society Colour Chart. The color values were determined on plant material grown as a pinched spray pot mum in Salinas, Calif. on Mar. 6, 1990.

Classification:

*Botanical*—*Dendranthema grandiflora* cv Rochelle.

*Commercial*—Spooned daisy spray pot mum.

INFLORESCENCE

A. Capitulum:

*Form*—Flat.

*Type*—Spooned daisy.

*Diameter across face*—38 to 44 mm. when fully opened.

B. Corolla of Ray Florets:

*Color (general tonality from a distance of three meters)*—Purple.

*Color*—Upper surface spoons: 75A to 75B. *Under surface tubes:* 75A. Base of tubes white.

*Shape*—Irregular flower form; spoons and tubes of different lengths. Most spoons are indented. Tubes are straight.

C. *Corolla of Disc Florets:*

*Color (mature)*—Closest to 154B.

*Color (immature)*—144A to 144B.

D. Reproductive Organs:

*Androecium*—Present on disc florets only; none to very scant pollen.

*Gynoecium*—Present on both ray and disc florets.

PLANT

A. General Appearance:

*Height*—18 to 25 cm. when grown as a pinched pot mum in a 15 cm. pot with 22 to 25 long days after direct sticking of unrooted cuttings and 1 to 2 applications of 2500 ppm B-9 SP.

*Branching pattern*—Spreading and prolific, with 5 to 7 laterals after pinch.

B. Foliage:

*Color (upper surface)*—147A.

*Color (under surface)*—147B.

*Shape*—See photograph.

CHART A

COMPARISON OF ROCHELLE AND PAPILLON

| CHARACTERISTIC | ROCHELLE | PAPILLON |
|---|---|---|
| Ray floret color | Purple | Red-purple |
| Capitulum form and type | Flat spooned daisy | Flat daisy |
| Diameter across face of capitulum | 38 to 44 mm. | 35 to 37 mm. |
| Flowering response | 44 to 52 days | 50 to 59 days |
| Branching pattern | Spreading 5 to 7 laterals | Spreading 4 to 6 laterals |

COMPARISONS MADE OF PLANTS GROWN AS PINCHED SPRAY POT MUMS IN SALINAS, CALIFORNIA

I claim:

1. A new and distinct Chrysanthemum plant named Rochelle, as described and illustrated.

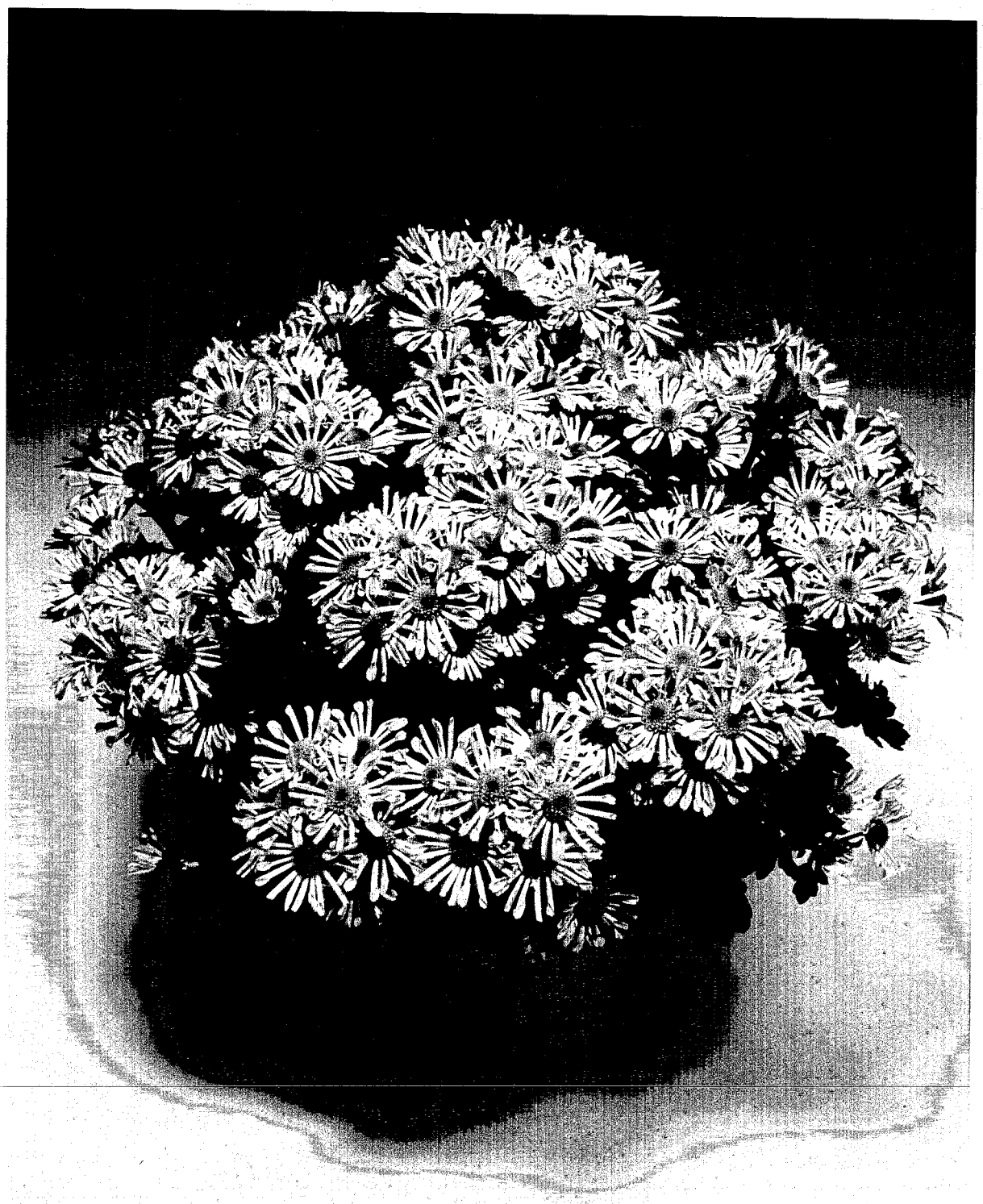

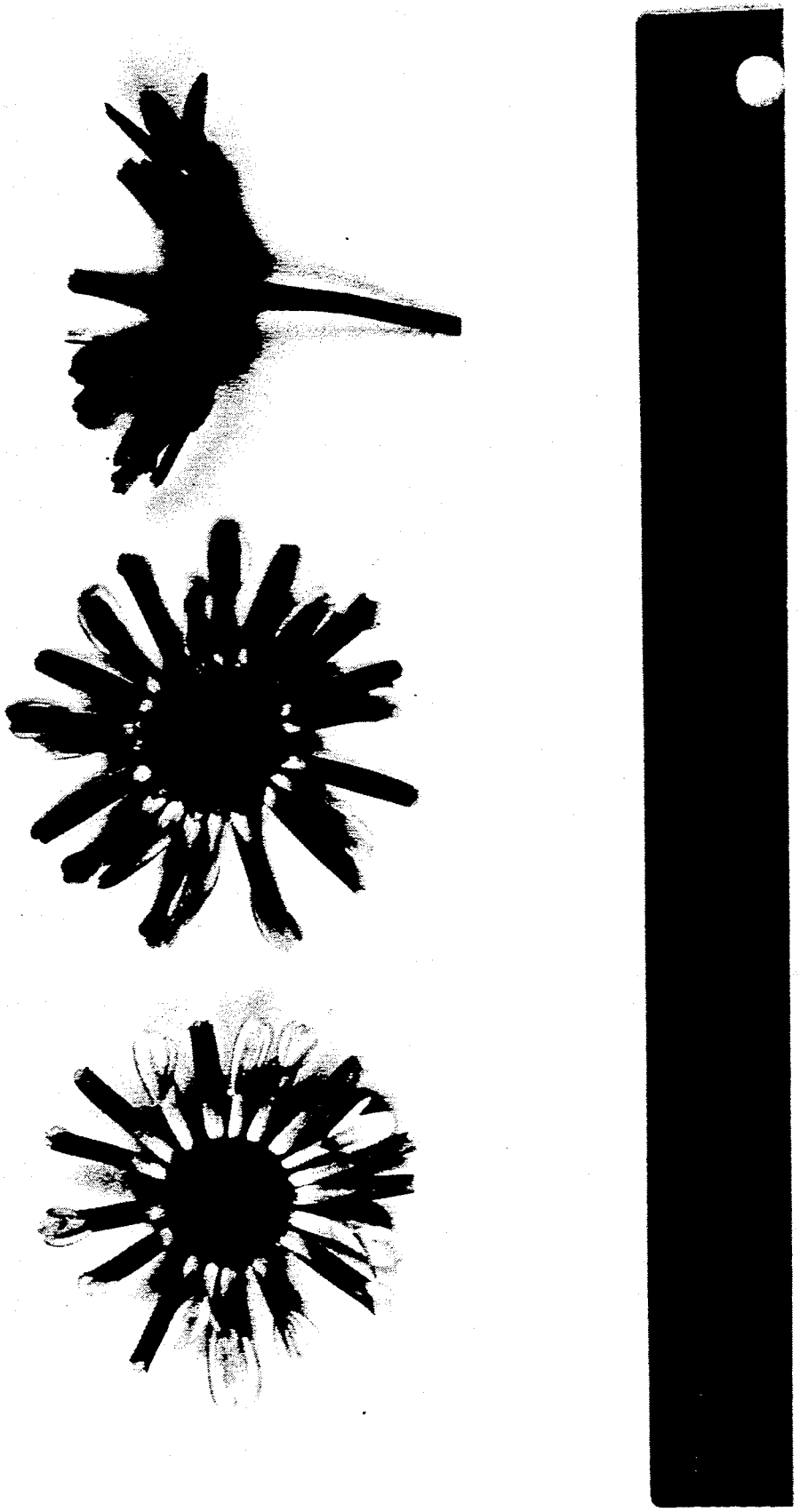

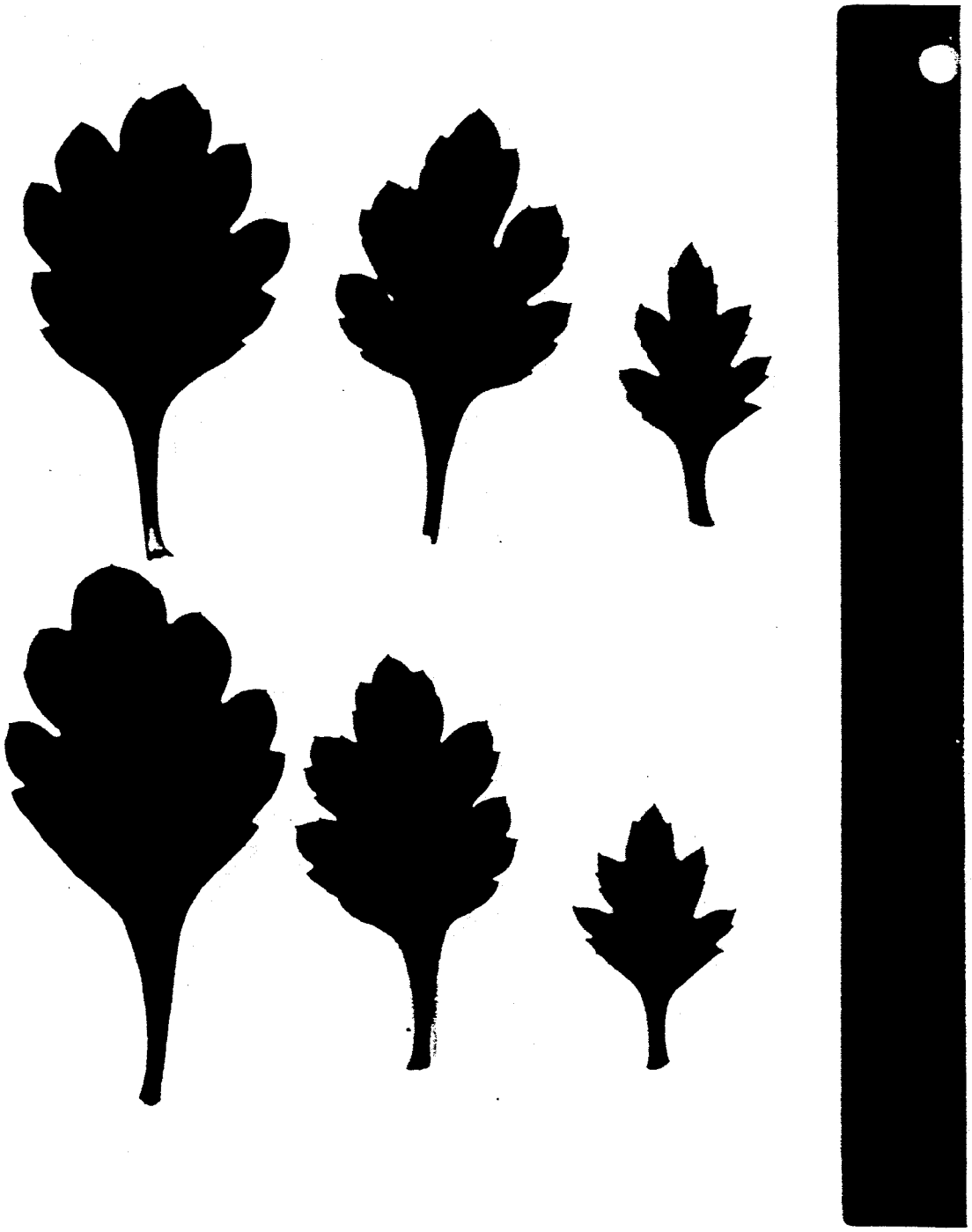

* * * * *